(12) United States Patent
Kontani et al.

(10) Patent No.: US 7,790,884 B2
(45) Date of Patent: Sep. 7, 2010

(54) ACYLAMINOPIPERIDINE COMPOUND

(75) Inventors: Toru Kontani, Tokyo (JP); Noriyuki Kawano, Tokyo (JP); Naoyuki Masuda, Tokyo (JP); Koji Kato, Tokyo (JP); Hiroshi Nagata, Tokyo (JP); Hiroshi Inami, Tokyo (JP); Tadashi Terasaka, Tokyo (JP); Kazuhiro Yokoyama, Tokyo (JP); Takahiro Miyazaki, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 92 days.

(21) Appl. No.: 12/294,145

(22) PCT Filed: Mar. 23, 2007

(86) PCT No.: PCT/JP2007/055943

§ 371 (c)(1),
(2), (4) Date: Sep. 23, 2008

(87) PCT Pub. No.: WO2007/111227

PCT Pub. Date: Oct. 4, 2007

(65) Prior Publication Data

US 2009/0131666 A1 May 21, 2009

(30) Foreign Application Priority Data

Mar. 24, 2006 (JP) .............................. 2006-084037

(51) Int. Cl.
*C07D 473/34* (2006.01)
(52) U.S. Cl. ...................................... 544/277; 544/293
(58) Field of Classification Search ................ 544/277, 544/293
See application file for complete search history.

(56) References Cited

U.S. PATENT DOCUMENTS

2004/0048865 A1   3/2004   Purandare

FOREIGN PATENT DOCUMENTS

| EP | 1 552 842 A1 | 7/2005 |
|----|--------------|--------|
| JP | 2005-162673 A | 6/2005 |
| JP | 2007-55940 A | 3/2007 |
| WO | 03/104230 A1 | 12/2003 |
| WO | 2005/082865 A1 | 9/2005 |
| WO | 2005/085212 A1 | 9/2005 |
| WO | 2005/123697 A1 | 12/2005 |

OTHER PUBLICATIONS

Philip M. Murphy, et al. "International Union of Pharmacology. XXII. Nomenclature for Chemokine Receptors", Pharmacological Reviews, vol. 52, No. 1, pp. 145-176.
A. J. Hoogewerf, et al. "Molecular Cloning of Murine CC CKR-4 and High Affinity Binding of Chemokines to Murine and Human CC CKR-4", Biochemical and Biophysical Research Communications, vol. 218, pp. 337-343 (1996).

Michel Samson, et al. "Molecular cloning and chromosomal mapping of a novel human gene, ChemR1, expressed in T lymphocytes and polymorphonuclear cells and encoding a putative chemokine receptor", Eur. J. Immunol, 1996. vol. 26, pp. 3021-3028.
David P. Andrew, et al. "C-C Chemokine Receptor 4 Expression Defines a Major Subset of Circulating Nonintestinal Memory T Cells of Both Th1 and Th2 Potential", The American Association of Immunologists, (2001), vol. 166, pp. 103-111.
Federica Sallusto, et al. "Flexible Programs of Chemokine Receptor Expression on Human Polarized T Helper 1 and 2 Lymphocytes", J. Exp. Med. © The Rockefeller University Press, vol. 187, No. 6, Mar. 16, 1998, pp. 875-883.
Chang H. Kim, et al. "Rules of chemokine receptor association with T cell polarization in vivo", The Journal of Clinical Investigation, vol. 108, pp. 1331-1339 (2001).
J. J. Campbell, et al. "The chemokine receptor CCR4 in vascular recognition by cutaneous but not intestinal memory Tcells", Letters to Nature, vol. 400, pp. 776-780, Aug. 19, 1999.
Kenneth J. Katschke, Jr., "Differential Expression of Chemokine Receptors on Peripheral Blood, Synovial Fluid, and Synovial Tissue Monocytes/Macrophages in Rheumatoid Arthritis", Arthritis & Rheumatism, vol. 44, No. 5, May 2001, pp. 1022-1032.
Toshio Imai, et al. "The T Cell-directed CC Chemokine TARC Is a Highly Specific Biological Ligand for CC Chemokine Receptor 4*", The Journal Of Biological Chemistry, vol. 272, No. 23, Jun. 6, 1997, pp. 15036-15042.

(Continued)

*Primary Examiner*—James O Wilson
*Assistant Examiner*—Brian McDowell
(74) *Attorney, Agent, or Firm*—Sughrue Mion, PLLC

(57) ABSTRACT

To provide a compound which has an excellent activity to modulate the functions of CCR4 or TARC and/or MDC and can be used for the prevention and/or treatment of various inflammatory diseases, allergic diseases, autoimmune diseases and the like.

An acylaminopiperidine compound represented by the formula (I) or a pharmaceutically acceptable salt thereof.

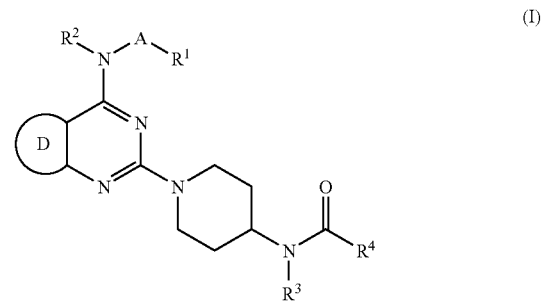

(I)

[Symbols in the formula represent the following meanings; A: a single bond or $C_1$-$C_6$ alkylene, $R^1$: phenyl which may be substituted, etc., $R^2$: —H or $C_1$-$C_6$ alkyl, $R^3$: —H, $C_1$-$C_6$ alkyl or $C_3$-$C_8$ cycloalkyl, $R^4$: pyrrolidin-2-yl which may be substituted, etc., and D: benzene ring or pyrazole ring].

2 Claims, No Drawings

OTHER PUBLICATIONS

Toshio Imai, et al. "Macrophage-derived Chemokine Is a Functional Ligand for the CC Chemokine Receptor 4*", The Journal Of Biological Chemistry, vol. 273, No. 3, Jan. 16, 1998, pp. 1764-1768.

Toshio Imai, et al. "Molecular Cloning of a Novel T Cell-directed CC Chemokine Expressed in Thymus by Signal Sequence Trap Using Epstein-Barr Virus Vector*", The Journal Of Biological Chemistry, vol. 271, No. 35, Aug. 30, 1996, pp. 21514-21521.

Ronald Godiska, et al. "Human Macrophage-derived Chemokine (MDC), a Novel Chemoattractant for Monocytes, Monocyte-derived Dendritic Cells, and Natural Killer Cells", J. Exp. Med. © The Rockefeller University Press, vol. 185, No. 9, May 5, 1997, pp. 1595-1604.

Alberto Mantovani "The chemokine system: redundancy for robust outputs", Immunology Today, vol. 20, No. 6, Jun. 1999, pp. 254-257.

Paola Panina-Bordignon, et al. "The C-C chemokine receptors CCR4 and CCR8 identify airway T cells of allergen-challenged atopic asthmatics", The Journal of Clinical Investigation, vol. 107, No. 11, Jun. 13, 2001, pp. 1357-1364.

Christian Vestergaard, et al. "A Th2 Chemokine, TARC, Produced by Keratinocytes May Recruit CLA+CCR4+ Lymphocytes into Lesional Atopic Dermatitis Skin", The Society for Investigative Dermatology, Inc., Jul. 2000, pp. 640-646.

James B. Rottman, et al. "Potential Role of the Chemokine Receptors CXCR3, CCR4, and the Integrin $\alpha E\beta 7$ in the Pathogenesis of Psoriasis Vulgaris", Laboratory Investigation, vol. 81, No. 3, pp. 335-347, Mar. 2001.

Jeffrey H. Ruth, et al. "Selective Lymphocyte Chemokine Receptor Expression in the Rheumatoid Joint", Arthritis & Rheumatism, vol. 44, No. 12, Dec. 2001, pp. 2750-2760.

Y. Jo, et al. "CCR4 is an up-regulated chemokine receptor of peripheral blood memory CD4+ T cells in Crohn's disease", Clin Exp Immunol, 2003, vol. 132, pp. 332-338.

ACYLAMINOPIPERIDINE COMPOUND

TECHNICAL FIELD

The present invention relates to a novel acylaminopiperidine compound and a pharmaceutical which comprises the same as an active ingredient, particularly an agent for treating inflammatory diseases, more illustratively an agent for treating rheumatism, psoriasis, atopic dermatitis and asthma.

BACKGROUND OF THE INVENTION

Chemokines which are the cell chemotactic factors are roughly classified into two types based on the structural characteristics, i.e., CXC/α chemokines and CC/β chemokines. Receptors of these chemokines belong to the 7-transmembrane G protein-coupled receptor family and are constituted by CXC chemokine receptors and CC chemokine receptors (Non-patent Reference 1).

CC chemokine receptor 4 (CCR4) was cloned from T lymphocyte and thymus (Non-patent Reference 2, Non-patent Reference 3) and reported to be expressed mainly in a T cell called Th2 type at the beginning (Non-patent Reference 4). However, it was shown by the detailed analyses thereafter that CCR4 is broadly present in the effector-memory T cells of Th1 and Th2 (Non-patent Reference 5, Non-patent Reference 6). According to further recent studies, it has been revealed that CCR4 is present in almost all of the skin-tropic T cells (Non-patent Reference 7) and monocyte, macrophage, dendritic cell and NK cell (Non-patent Reference 8).

Thymus and activation-regulated chemokine (TARC) and macrophage-derived chemokine (MDC) as CC chemokines are specific ligands for CCR4 (Non-patent Reference 9, Non-patent Reference 10). The TARC was found as a T cell chemotactic factor (Non-patent Reference 11), and the MDC as a chemotactic factor of monocyte, macrophage and NK cell (Non-patent Reference 12). It is known that both of the chemokines have characteristics of both inflammatory chemokine and homeostatic chemokine (Non-patent Reference 13).

It has been suggested by a large number of reports that CCR4 and its ligands TARC and MDC are concerned in various diseases such as inflammatory diseases, allergic diseases, autoimmune diseases and the like. For example, asthma (Non-patent Reference 14), atopic dermatitis (Non-patent Reference 15), psoriasis (Non-patent Reference 16), rheumatoid arthritis (Non-patent Reference 17), inflammatory bowel disease (Non-patent Reference 18) and the like may be exemplified. Accordingly, an agent that modulates the functions of CCR4 is expected as an agent for preventing or treating these diseases and the like. As the agents for preventing or treating the above-mentioned inflammatory diseases, allergic diseases, autoimmune diseases and the like, various drugs such as steroid agents and the like are used. From the viewpoint of their therapeutic effects and side effects, great concern has been directed toward the development of a drug based on a new functional mechanism.

For example, it has been reported that a compound represented by the following formula has an activity to modulate the functions of TARC or MDC (Patent Reference 1).

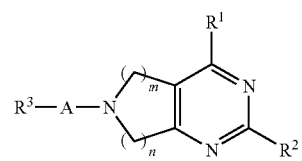

[See said reference for symbols in the formula.]

Also, it has been reported that, for example, a compound represented by the following formula has an activity to modulate the functions of CCR4 (Patent Reference 2).

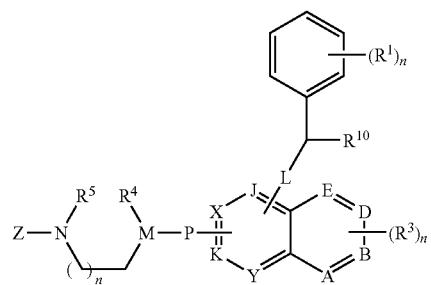

[See said reference for symbols in the formula.]

Also, it has been reported that a compound represented by the following formula has an activity to modulate the functions of CCR4 (Patent Reference 3).

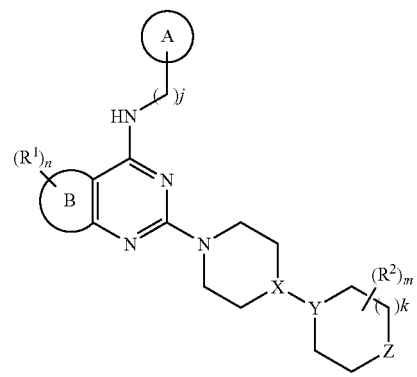

[See said official gazette for symbols in the formula.]

Also, it has been reported that a compound represented by the following formula has an activity to modulate the functions of CCR4 (Patent Reference 4).

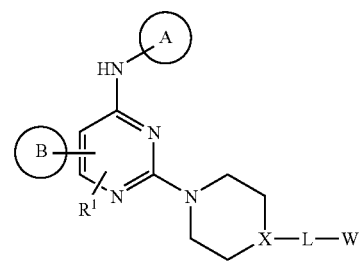

[See said reference for symbols in the formula.]

In addition, it has been reported that a compound represented by the following formula has the action to modulate function of CCR4 (Patent Reference 5).

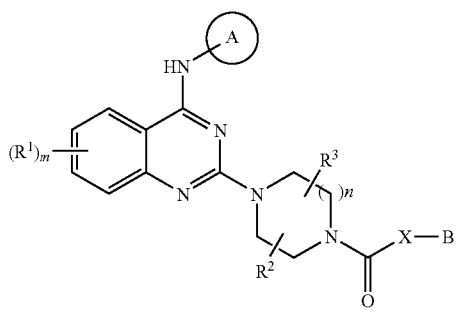

[See said reference for symbols in the formula.]

However, there is no disclosure or suggestion in any one of the above-mentioned references on the acylaminopiperidine compound according to the present invention.

Non-patent Reference 1: Pharmacological Reviews, 52, 145, 2000

Non-patent Reference 2: Biochemical and Biophysical Research Communications, 218, 337, 1996

Non-patent Reference 3: European Journal of Immunology, 26, 3021, 1996

Non-patent Reference 4: Journal of Experimental Medicine, 187, 875, 1998

Non-patent Reference 5: Journal of Immunology, 166, 103, 2001

Non-patent Reference 6: The Journal of Clinical Investigation, 108, 1331, 2001

Non-patent Reference 7: Nature, 400, 776, 1999

Non-patent Reference 8: Arthritis & Rheumatism, 44, 1022, 2001

Non-patent Reference 9: Journal of Biological Chemistry, 272, 15036, 1997

Non-patent Reference 10: Journal of Biological Chemistry, 273, 1764, 1998

Non-patent Reference 11: Journal of Biological Chemistry, 271, 21514, 1996

Non-patent Reference 12: Journal of Experimental Medicine, 185, 1595, 1997

Non-patent Reference 13: Immunology Today, 20, 254, 1999

Non-patent Reference 14: The Journal of Clinical Investigation, 107, 1357, 2001

Non-patent Reference 15: Journal of Investigative Dermatology, 115, 640, 2000

Non-patent Reference 16: Laboratory Investigation, 81, 335, 2001

Non-patent Reference 17: Arthritis & Rheumatism, 44, 2750, 2001

Non-patent Reference 18: Clinical & Experimental Immunology, 132, 332, 2003

Patent Reference 1: International Publication WO 03/104230

Patent Reference 2: US Patent Publication 2004/0048865

Patent Reference 3: International Publication WO 2005/082865

Patent Reference 4 International Publication WO 2005/085212

Patent Reference 5: International Publication WO 2005/123697

DISCLOSURE OF THE INVENTION

Problems that the Invention is to Solve

The present inventors have conducted studies with the aim of providing a pharmaceutical composition useful for preventing and/or treating inflammatory diseases, allergic diseases, autoimmune disease and the like, based on the activity to modulate the functions of CCR4, and of further providing a medicament comprising the same.

The inventors have conducted extensive studies on the compounds having an activity to modulate the functions of CCR4 and, as a result, found that a novel acylaminopiperidine compound is useful as an agent for modulating the functions of CCR4, and thereby accomplished the present invention.

That is, according to the present invention, there is provided a novel acylaminopiperidine compound represented by the following formula (I) or a pharmaceutically acceptable salt thereof

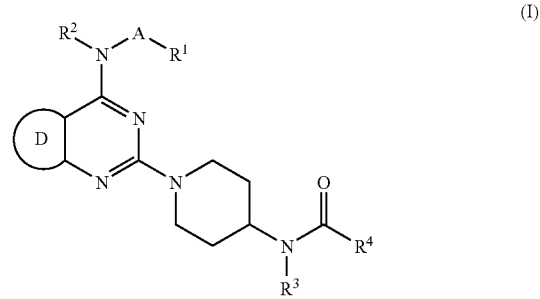

[symbols in the formula represent the following meanings;

A: a single bond or $C_1$-$C_6$ alkylene, $R^1$: phenyl which may be substituted or pyridyl which may be substituted, $R^2$: —H or $C_1$-$C_6$ alkyl, $R^3$: —H, $C_1$-$C_6$ alkyl or $C_3$-$C_8$ cycloalkyl, $R^4$: azetidin-2-yl, pyrrolidin-2-yl or piperidin-2-yl, each of which may be substituted, and D: a ring selected from the group consisting of the following rings, wherein in these rings, the carbon atoms and nitrogen atoms constituting the rings may respectively be substituted,

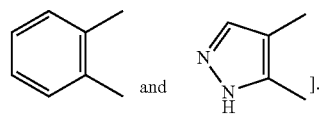

In this connection, preferred as A in the formula (I) is a single bond or $C_1$-$C_2$ alkylene, more preferred is a single bond or methylene and further preferred is a single bond. Also, preferred as —$R^1$ is phenyl which may be substituted; preferred as —$R^2$ is —H; preferred as —$R^3$ is —H, $C_1$-$C_2$ alkyl or $C_3$-$C_4$ cycloalkyl; and preferred as —$R^4$ is pyrrolidin-2-yl which may be substituted.

In addition, preferred among these compounds is a compound in which $R^2$ is —H and $R^4$ is pyrrolidin-2-yl which may be substituted.

The compound of the present invention represented by the formula (I) has a structural characteristic in that the 1-position of the piperidine, of which the 4-position is substituted with an acylamino group, is linked to the 2-position of the fused pyrimidine, and has a pharmacological characteristic in that it has an activity to modulate the functions of CCR4.

EFFECTS OF THE INVENTION

Since the acylaminopiperidine compound of the present invention has the activity to modulate functions of CCR4 or TARC and/or MDC, it is useful as an agent for preventing and/or treating various inflammatory diseases, allergic diseases, autoimmune diseases and the like. Illustrative diseases include asthma, allergic rhinitis, allergic conjunctivitis, pollinosis, dermatitis (atopic dermatitis, contact dermatitis), psoriasis, rheumatoid arthritis, systemic lupus erythematosus, multiple sclerosis, insulin-dependent diabetes (type 1 diabetes) rejection at the time of organ transplantation, cancer, inflammatory bowel disease (ulcerative colitis, Crohn disease), interstitial cystitis, sepsis, pain and the like. Particularly, it is expected as an agent for preventing and/or treating asthma, atopic dermatitis or rheumatoid arthritis.

BEST MODE FOR CARRYING OUT THE INVENTION

The present invention is further described below.

In this description, the "alkyl" means a monovalent group of a straight or branched carbon chain. Accordingly, illustrative examples of "$C_1$-$C_6$ alkyl" include methyl, ethyl, n-propyl, isopropyl, n-butyl, isobutyl, t-butyl, n-pentyl, neopentyl, n-hexyl and the like, of which a $C_1$-$C_3$ alkyl, or methyl, ethyl, n-propyl or isopropyl is preferable.

In addition, the "alkylene" means a divalent group of a straight or branched carbon chain. Thus, illustrative examples of the "$C_1$-$C_6$ alkylene" include methylene, ethylene, n-propylene, methylethylene, 1,1-dimethylmethylene, n-butylene, 1,2-dimethylethylene, 1,1-dimethylethylene, ethylethylene, n-pentylene, n-hexylene and the like, of which a $C_1$-$C_3$ alkylene, or methylene, ethylene, n-propylene, methylethylene or 1,1-dimethylmethylene, is preferable.

In the present description, the acceptable substituent of the terms "may be substituted" and "substituted" may be any substituent which is generally used as the substituent of respective groups. In addition, two or more of these substituents may be present on each group.

As the acceptable substituent for the "phenyl which may be substituted or pyridyl which may be substituted" of —$R^1$, halogen and cyano can be exemplified. The "halogen" is fluoro, chloro, bromo or iodo, preferably fluoro, chloro, bromo, more preferably fluoro or chloro (the same shall apply hereinafter).

As the acceptable substituent for the "azetidin-2-yl, pyrrolidin-2-yl or piperidin-2-yl which may be respectively substituted" of —$R^4$, —OH, —O—$C_1$-$C_6$ alkyl, oxo (═O) or —$SO_2$—$C_1$-$C_6$ alkyl, or $C_1$-$C_6$ alkyl which may be substituted with a group selected from the class consisting of —OH, —O—$C_1$-$C_6$ alkyl and oxo (═O) can be exemplified.

As the acceptable substituent for the "in these rings, the carbon atoms and nitrogen atoms constituting the rings may respectively be substituted" of D, halogen, cyano or —O—$C_1$-$C_6$ alkyl, or $C_1$-$C_6$ alkyl which may be substituted with a group selected from the class consisting of —OH, —O—$C_1$-$C_6$ alkyl and halogen can be exemplified.

There are cases in which geometrical isomers and tautomers are present in the compound (I) of the present invention depending on the kind of substituents. Also, the compound (I) of the present invention may have asymmetric carbon atom in some cases. The present invention includes separated forms of these isomers or mixtures thereof. In addition, a labeled substance, namely a compound in which at least one atom of the compound of the present invention is replaced by a radioisotope or non-radioactive isotope, is also included in the present invention.

Further, a pharmacologically acceptable so-called prodrug is also included in the compound (I) of the present invention. The pharmacologically acceptable prodrug is a compound which has a group that can be converted into the amino group, hydroxyl group, carboxyl group or the like of the present invention by solvolysis or under a physiological condition, and as the group which forms such a prodrug, the groups described in Prog. Med., vol. 5, pp. 2157-2161, 1985, and in "Iyakuhin no Kaihatsu (Development of Medicines)" (Hirokawa Shoten, 1990) vol. 7 Bunshi Sekkei (Molecular Design), pp. 163-198, can be exemplified.

There are cases in which the compound (I) forms an acid addition salt or a salt with a base depending on the kind of substituents. Such a salt can be any salt which is pharmaceutically acceptable, and illustratively, an acid addition salt with inorganic acids include hydrochloric acid, hydrobromic acid, hydriodic acid, sulfuric acid, nitric acid, phosphoric acid and the like, or organic acids include formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like, or salts with inorganic bases include sodium, potassium, magnesium, calcium, aluminum and the like, or with organic bases include methylamine, ethylamine, ethanolamine, lysine, ornithine and the like, or ammonium salts or the like can be exemplified.

In addition, the present invention also includes various hydrates and solvates and crystal polymorph of the compound (I) of the present invention or a salt thereof.

(Production Methods)

The compound (I) as an active ingredient of the present invention and a pharmaceutically acceptable salt thereof can be produced by employing various conventionally known synthesis methods making use of the characteristics based on its basic skeleton or kind of the substituents. In that case, depending on the kind of functional group, there is an effective case from the production technology point of view to protect said functional group with an appropriate protecting group at the stage of materials to intermediates, or to replace it with a group which can be easily converted into said functional group. Examples of such a functional group include amino group, hydroxyl group, carboxyl group and the like, and as their protecting groups, the protecting groups described for example in "Protective Groups in Organic Synthesis" edited by T. W. Greene and P. G. M. Wuts, ($3^{rd}$ edition, 1999)" can be exemplified, which may be optionally selected and used in response to the reaction conditions. According to such a method, a desired compound can be obtained by introducing said protecting group and carrying out the reaction, and then removing the protecting group as occasion demands, or converting it into a desired group.

In addition, the prodrug of the compound (I) of the present invention can be produced in the same manner as the case of the above-mentioned protecting groups, by carrying out the reaction after introducing a specific group at the stage of materials to intermediates or using the obtained compound (I). The reaction can be carried out by employing methods known to one skilled in the art, such as usual esterification, amidation, dehydration and the like.

<First Production Method>

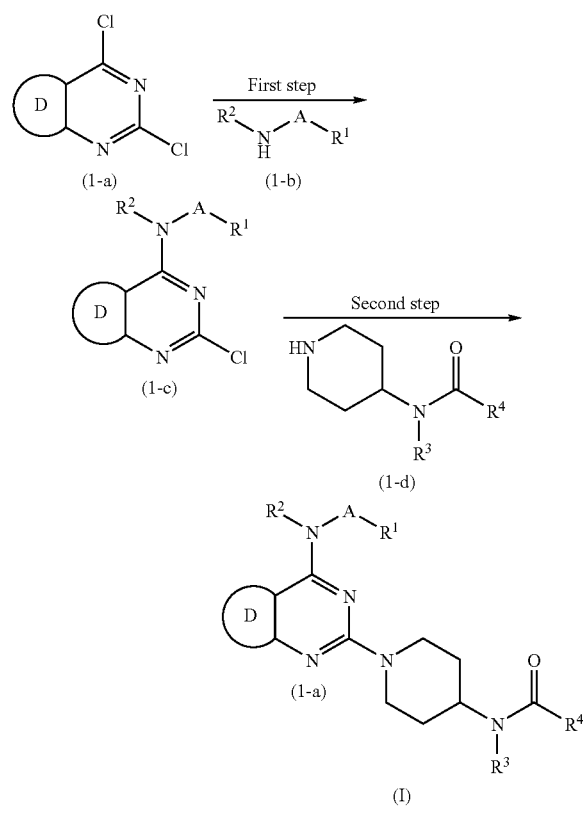

(In the formulae, A, —R$^1$, —R$^2$, —R$^3$, —R$^4$ and D are as defined in the foregoing. The same shall apply hereinafter.)

This production method is a method in which the compound (I) of the present invention is produced by allowing the amine derivative represented by (1-b) to react with the dichloropyrimidine represented by (1-a) which is thereby converted into the aminochloropyrimidine represented by (1-c) (first step), and further allowing the piperidine derivative represented by (1-d) to react therewith (second step).

Both of the first step and second step are carried out under ordinary pressure or pressurization, in the absence of a solvent or in an appropriate solvent.

As illustrative examples of the solvent, aromatic hydrocarbons such as toluene, xylene and the like; ketones such as acetone, methyl ethyl ketone and the like; ethers such as ether, tetrahydrofuran (THF), dioxane, diethoxyethane and the like; alcohols such as methanol (MeOH), ethanol (EtOH), 2-propanol (iPrOH) and the like; aprotic polar solvents such as acetonitrile; dimethylformamide (DMF), 1,3-dimethyl-2-imidazolidinone, dimethyl sulfoxide (DMSO) and the like; water; or a mixed solvent thereof can be exemplified. It is preferable to carry out this reaction in the presence of a base, and illustrative examples of the base include alkali carbonates such as sodium carbonate, potassium carbonate and the like; alkali bicarbonates such as sodium bicarbonate, potassium bicarbonate and the like; alkoxides such as sodium methoxide, sodium ethoxide, potassium t-butoxide and the like; tertiary amines such as triethylamine, diisopropyl ethylamine and the like; other organic bases such as 1,8-diazabicyclo [5.4.0]undec-7-ene, pyridine, lutidine and the like. Excess amount of (1-d) can also serve as the base. The reaction temperature varies depending on the kinds of material compounds, reaction conditions and the like, but it can be carried out in general at approximately from room temperature to reflux temperature of the solvent.

In this connection, the production materials (1-b) and/or (1-d) can be subjected to the reaction as a salt thereof. In addition, the production material (1-a) can be easily produced by the method described in the reference examples of this description, or for example by the method described in the aforementioned Patent Reference 4 or 6, or a method in accordance therewith.

<Production Method for Intermediate>

In this connection, the piperidine derivative represented by (1-d) to be used in the second step of the first production method can be produced by the method shown below.

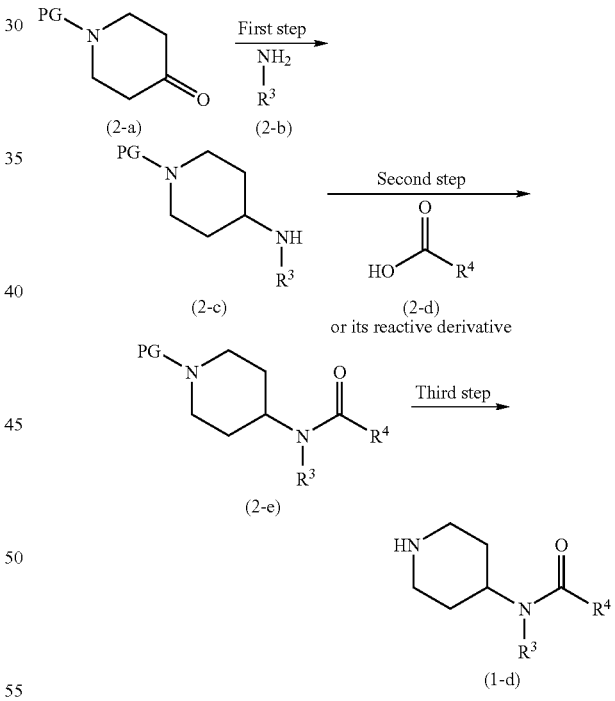

(In the formulae, PG represents a protecting group of amino group. The same shall apply hereinafter.)

As the protecting group of amino group, the protecting groups described in the aforementioned "Protective Groups in Organic Synthesis (3$^{rd}$ edition, 1999)" can be exemplified, and illustratively, for example, tert-butoxycarbonyl, benzyloxycarbonyl and the like can be exemplified.

This production method is a method in which the piperidine derivative represented by (1-d) to be used in the second step of the first production method is produced by allowing the amine derivative represented by (2-b) to react with the piperidine derivative represented by (2-a) which can be easily obtained (first step), thereby converting into an amino piperidine represented by (2-c), further allowing it to react with the carboxylic acid represented by (2-d) or a reactive derivative thereof (second step), thereby converting into an acylaminopiperidine derivative represented by (2-e), and further carrying out deprotection of the 1-position of piperidine (third step).

It is preferable that the first step uses a reductive amination reaction. For example, the methods described in "Jikken Kagaku Koza (Experimentation Chemistry Course) ($4^{th}$ edition)" edited by The Chemical Society of Japan, vol. 20 (1992) (Maruzen) and the like, the methods obvious to those skilled in the art or modified methods thereof can be used.

The second step can be carried out under cooling, under cooling to room temperature or under room temperature to heating, preferably under room temperature, using equivalent amount of (2-c) and (2-d), or one of them in an excess amount, in the presence of a condensing agent such as dicyclohexylcarbodiimide (DCC), diisopropylcarbodiimide (DIPC), 1-ethyl-3-(3-dimethylaminopropyl)carbodiimide (EDCI), 1,1-carbonylbis-1H-imidazole (CDI) or the like and, as occasion demands, an additive agent such as N-hydroxysuccinimide (HONSu), 1-hydroxybenzotriazole (HOBt) or the like. Illustrative examples of the solvent include ethers; halogenated hydrocarbons such as dichloromethane, 1,2-dichloroethane, chloroform and the like; acetonitrile; aprotic polar solvents such as dimethylformamide (DMF), 1,3-dimethyl-2-imidazolidinone, dimethyl sulfoxide (DMSO) and the like; or a mixed solvent thereof. In addition, it is also advantageous in some cases to carry out in the presence of a base such as triethylamine, diisopropylethylamine, pyridine or the like.

The method described in the deprotection reaction of amino group and the like of the aforementioned "Protective Groups in Organic Synthesis ($3^{rd}$ edition, 1999)" may be used in the third step.

In addition, some of the compounds represented by the formula (I) may also be produced from the compound of the present invention produced in the above manner, by optionally combining known steps which are generally employed by those skilled in the art, such as alkylation, acylation, substitution reaction, oxidation, reduction, hydrolysis, deprotection and the like.

The reaction product obtained by the above-mentioned each production method is isolated and purified as a free compound, a salt thereof or various types of solvate such as hydrate or the like. The salt can be produced by subjecting to a general salt formation treatment.

The isolation and purification are carried out by employing general chemical operations such as extraction, concentration, evaporation, crystallization, filtration, recrystallization, various types of chromatography and the like.

Various isomers can be isolated in the usual way, by making use of the difference in physicochemical properties between the isomers. For example, optical isomers can be separated by a general optical resolution method such as fractional crystallization, chromatography or the like. In addition, an optical isomer can also be produced from an appropriate optically active material compound.

Pharmacological activities of the compound of the present invention were verified by the following tests.

1. Action for [$^{35}$S]GTPγS Binding Test Via CCR4

(1) Preparation of Human CCR4 Expressing Cell Line

A vector (contains a neomycin-resistance gene) in which human CCR4 gene was inserted into downstream of the EF-1α promoter was prepared and transfected into a mouse pre B cell line B300-16 cells by electroporation. These cells were cultured using a G-418-supplemented medium, and a single cell line capable of producing human CCR4 constantly and stably was obtained by the limiting dilution method.

(2) Preparation of Human CCR4 Expressing Cell Line Membrane Fraction

The human CCR4 expressing cells were recovered, washed with PBS and then suspended in a lysis buffer (10 mM HEPES pH 7.5, 2 mM EDTA, proteinase inhibitor). After allowing the suspension to stand on ice for 15 minutes, the cells were disintegrated using a homogenizer and centrifuged (2000 rpm, 10 min, 4° C.). The supernatant was further subjected to ultracentrifugation (22 K, 30 min, 4° C.), and then the pellet was suspended in PBS and used in the subsequent test.

(3) GTPγS Binding Test

In a reaction mixture liquid containing 20 mM of HEPES pH 7.05, 100 mM of NaCl, 5 mM of $MgCl_2$, 2 μM of GDP, human MDC, 150 μM of [$^{35}$S]GTPγS, 1 mg of wheat germ agglutinin SPA beads and 1 μg of the human CCR4 expressing cell line membrane fraction, respective concentration of the test compound was allowed to undergo the reaction at room temperature for 1 hour and 30 minutes, and the radioactivity was measured.

As a result, the compounds of Example 1, Example 2, Example 5, Example 6, Example 7, Example 9, Example 10, Example 12, Example 13, Example 15, Example 16, Example 17, Example 19, Example 20, Example 21, Example 22, Example 24, Example 26, Example 27, Example 28, Example 29, Example 30, Example 31, Example 32, Example 33, Example 35, Example 36, Example 37, Example 38, Example 39, Example 40, Example 41, Example 42, Example 43, Example 44, Example 45, Example 46, Example 47, Example 48, Example 49, Example 50, Example 51, Example 53, Example 54, Example 55, Example 56, Example 57, Example 58, Example 59, Example 60, Example 61, Example 62, Example 63, Example 64, Example 65, Example 66, Example 67, Example 68, Example 69, Example 70, Example 72, Example 73, Example 74, Example 75, Example 76, Example 77, Example 78, Example 79, Example 80, Example 86, Example 87, Example 90, Example 91, Example 92, Example 95, Example 99, Example 100, Example 101, Example 102, Example 103, Example 104, Example 105 and Example 106 showed an inhibitory activity value ($IC_{50}$) of 100 nM or less.

2. Action Upon Mouse Oxazolone-Induced Contact Dermatitis

Balb/c mice (6 to 10 weeks of age, female, Charles River Japan) were sensitized by applying 150 μl of 3% oxazolone/ethanol solution (Sigma Aldrich Japan) to the abdominal part. On the $6^{th}$ day after the sensitization, 10 μl of 1% oxazolone/ethanol solution was applied to both sides of the right ear. The test drug was administered in 12 hours after the application of the oxazolone solution (test drug administration group), and the solvent alone used in dissolving the test drug was administered to the control group. Thickness of the right auricle was measured before the application and 20 hours thereafter using a sickness gauge (Mitsutoyo), and the swelling (thickness increment=measured value after 20 hours–measured value before application) was calculated. The inhibition ratio was calculated by the following formula, by regarding a group to which the oxazolone solution was applied without sensitization as the normal group. In this connection, the above-mentioned test was carried out by 5 animals per group.

Inhibition ratio=(swelling of control group−swelling of test drug administration group)×100/(swelling of control group−swelling of normal group)

As a result, the compound of Example 1 showed good inhibitory activity by 30 mg/kg oral administration.

3. Action Upon Mouse Collagen-Induced Arthritis

The action upon mouse collagen-induced arthritis can be evaluated using the method described in The Japanese Journal of Pharmacology, 88, 332 (2002).

In addition to the above-mentioned respective test example, pharmacological actions of the compound of the present invention can be verified by various evaluation models generally used for the evaluation of anti-inflammation actions, such as the mice asthma model described in Immunology, 98, 345 (1999), the oxazolone-induced chronic contact dermatitis model (atopic dermatitis model) described in Journal of Investigative Dermatology, 111, 86 (1998) and the like.

It was confirmed from the above test results that the compound of the present invention has the function modulating action of CCR4 or TARC and/or MDC and therefore is useful as an agent for preventing and treating various inflammatory diseases, allergic diseases, autoimmune diseases and the like.

The pharmaceutical preparation which comprises one or two or more species of the compound (I) or a salt thereof as the active ingredient is prepared using carriers, fillers and other additive agents, which are generally used in preparing medicines.

The administration may be either oral administration by tablets, pills, capsules, granules, powders, solutions and the like, or parenteral administration by injections (e.g., intravenous, intramuscular and the like), suppositories, transdermal preparations, transnasal preparations, inhalations and the like. The dose is optionally decided in response to each case by taking symptoms and age, sex and the like of the object to be administered into consideration, but is generally approximately from 0.001 mg/kg to 100 mg/kg per day per adult in the case of oral administration, and this is administered once or by dividing into 2 to 4 doses. Also, in the case of intravenous administration due to the symptom, it is administered generally once to 2 or more times a day within a range of from 0.0001 mg/kg to 10 mg/kg per once per adult. Also, in the case of inhalation, it is administered generally once to 2 or more times a day within a range of from 0.0001 mg/kg to 1 mg/kg per once per adult.

As the solid composition for oral administration by the present invention, tablets, powders, granules and the like are used. In such a solid composition, one or two more of active substances are mixed with at least one inert filler such as lactose, mannitol, glucose, hydroxypropylcellulose, microcrystalline cellulose, starch, polyvinyl pyrrolidone, aluminum magnesium silicate or the like. In accordance with the usual way, the composition may contain inert additive agents such as lubricants (e.g., magnesium stearate and the like), disintegrators (e.g., carboxymethylstarch sodium and the like), and solubilizing agents. As occasion demands, the tablets or pills may be coated with a sugar coating or a gastric or enteric coating.

The liquid composition for oral administration includes pharmaceutically acceptable emulsions, solutions, suspensions, syrups, elixirs and the like, and contains a generally used inert solvent such as purified water or ethanol. In addition to the inert solvent, this composition may contain auxiliary agents (e.g., solubilizing agents, moistening agents, suspending agents and the like), and sweeteners, correctives, aromatics and antiseptics.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oils (e.g., olive oil or the like), alcohols (ethanol or the like), polysorbate 80 (the name in Pharmacopeia) and the like. Such a composition may further contain tonicity agents, antiseptics, moistening agents, emulsifying agents, dispersing agents, stabilizing agents and solubilizing agents. These are sterilized by, for example, filtration through a bacteria retaining filter, formulation of bactericides or irradiation. In addition, these can also be used by producing a sterile solid composition and dissolving or suspending it in sterile water or a sterile solvent for injection prior to use.

Transmucosal preparations (e.g., inhalations, transnasal preparations and the like) are used in a solid, liquid or semi-solid form and can be produced in accordance with conventionally known methods. For example, an excipient such as lactose, starch or the like, as well as a pH adjusting agent, an antiseptic, a surfactant, a lubricant, a stabilizer, a thickener and the like, may be optionally added. An appropriate device for inhalation or blowing can be used for the administration. For example, using a known device such as the measured administration inhalation device or the like or a sprayer, a compound can be administered alone or as a powder of a formulated mixture, or as a solution or suspension by a combination with a medicinally acceptable carrier. The dry powder inhaler or the like may be for single or multiple administration use, and a dry powder or a powder-containing capsule can be used. Alternatively, it may be a pressurized aerosol spray or the like form which uses chlorofluoroalkane, hydrofluoroalkane or carbon dioxide or the like suitable gas.

As the external preparations, ointments, hard cream preparations, creams, jellies, cataplasmas, sprays, lotions, eye drops, eye ointments and the like are included. Generally used ointment base, lotion base, aqueous or non-aqueous solutions, suspensions, emulsions and the like are contained therein. For example, polyethylene glycol, carboxyvinyl polymer, white petrolatum, white beeswax, polyoxyethylene hydrogenated castor oil, glyceryl monostearate, stearyl alcohol, cetyl alcohol, lauromacrogol, sorbitan sesquioleate and the like can be exemplified as the ointment or lotion base.

EXAMPLES

The following describes the present invention in detail based on Examples. The present invention is not limited to the invention of compounds described in the following Examples. In addition, production methods of the starting compounds are shown in the reference examples.

Reference Example 1

In the presence of 1,8-diazabicyclo[5.4.0]undec-7-ene, tert-butyl methyl(piperidin-4-yl)carbamate was allowed to react with a 1,4-dioxane solution of 2-chloro-N-(4-chloro-2-fluorophenyl)-6,7-dimethoxyquinazoline-4-amine to convert into tert-butyl (1-{4-[(4-chloro-2-fluorophenyl)amino]-6,7-dimethoxyquinazolin-2-yl}piperidin-4-yl)methylcarbamate.

Subsequently, trifluoroacetic acid was added thereto to obtain N-(4-chloro-2-fluorophenyl)-6,7-dimethoxy-2-[4-(methylamino)piperidin-1-yl]quinazoline-4-amine.

ES: 446.

The compounds shown in Table 1 were produced in the same manner as in the method of Reference Example 1.

In this connection, symbols in the table represent the following meanings (the same shall apply hereinafter).

Rf: Reference example number.

CS: Chemical structural formula (In the chemical structural formula, Me represents methyl, and MeO methoxy and Et ethyl).

Data: Physical data (F: FAB-MS (M+H)$^+$, ES: ESI-MS (M+H)$^+$, NMR: NMR data (δ (ppm) of characteristic peak in $^1$H-NMR when tetramethylsilane was used as the internal standard, and DMSO-$d_6$ as the measuring solvent).

TABLE 1

| Rf | CS | Data |
|---|---|---|
| 1-1 | | ES: 432. |
| 1-2 | | F: 411. |
| 1-3 | | ES: 472. |
| 1-4 | | ES: 460. |
| 1-5 | | ES: 434. |
| 1-6 | | ES: 486. |

Reference Example 2

Cyclopropylamine and sodium triacetoxy borohydride were added to a 1,2-dichloromethane solution of benzyl 4-oxopiperidine-1-carboxylate to obtain benzyl 4-(cyclopropylamino)piperidine-1-carboxylate.

Next, by allowing this to react with bis-tert-butyl dicarbonate, benzyl 4-[(tert-butoxycarbonyl)(cyclopropyl)amino]piperidine-1-carboxylate was obtained.

ES: 375.

The compounds shown in Table 2 were produced in the same manner as in the method of Reference Example 2.

Symbols in the chemical structural formulae represent the following meanings (the same shall apply hereinafter). Z: Benzyloxycarbonyl, Boc: tert-butyloxycarbonyl.

TABLE 2

| Rf | CS | Data |
|---|---|---|
| 2-1 | Z-N-piperidine-N(Boc)-cyclobutyl | F: 389. |
| 2-2 | HN-piperidine-N(Boc)-cyclopropyl | |
| 2-3 | HN-piperidine-N(Boc)-cyclobutyl | |

Reference Example 3

By allowing benzyl 4-(methylamino)piperidine-1-carboxylate to react with EDCI hydrochloride, HOBt and 1-(tert-butoxycarbonyl)-L-proline, benzyl 4-[[1-(tert-butoxy)-L-prolyl](methyl)amino]piperidine-1-carboxylate was obtained.

F: 446.

The compounds shown in Table 3 were produced in the same manner as in the method of Reference Example 3.

TABLE 3

| Rf | CS | Data |
|---|---|---|
| 3-1 | Z-N-piperidine-N(Me)-C(O)-prolyl-Boc | F: 446. |
| 3-2 | Z-N-piperidine-N(Et)-C(O)-prolyl-Boc | F: 460. |
| 3-3 | Z-N-piperidine-N(Et)-C(O)-prolyl-Boc | F: 460. |

Reference Example 4

A mixture of benzyl 4-[[1-(tert-butoxy)-L-prolyl](methyl)amino]piperidine-1-carboxylate, 10% palladium carbon and ethanol was stirred under the atmosphere of hydrogen to obtain tert-butyl (2S)-2-{[methyl(piperidin-4-yl)amino]carbonyl}pyrrolidine-1-carboxylate.

F: 312.

The compounds shown in Table 4 were produced in the same manner as in the method of Reference Example 4.

TABLE 4

| Rf | CS | Data |
|---|---|---|
| 4-1 | HN-piperidine-N(Me)-C(O)-prolyl-Boc | F: 312. |
| 4-2 | HN-piperidine-N(Et)-C(O)-prolyl-Boc | F: 326. |
| 4-3 | HN-piperidine-N(Et)-C(O)-prolyl-Boc | F: 326. |

Reference Example 5

By allowing tert-butyl 4-(methylamino)piperidine-1-carboxylate to react with EDCI hydrochloride, HOBt and 1-methyl-L-proline, tert-butyl 4-[methyl(1-methyl-L-prolyl)amino]piperidine-1-carboxylate was obtained. Then, trifluoroacetic acid was added thereto to obtain N,1-dimethyl-N-piperidin-4-yl-L-prolinamide.

ES: 226.

The compounds shown in Table 5 were produced in the same manner as in the method of Reference Example 5.

TABLE 5

| Rf | CS | Data |
|---|---|---|
| 5-1 | HN-piperidine-N(Me)-C(O)-prolyl-Me | ES: 226. |
| 5-2 | HN-piperidine-N(Et)-C(O)-prolyl-Me | ES: 240. |

TABLE 5-continued

| Rf | CS | Data |
|---|---|---|
| 5-3 | (structure: piperidine-NH with C(=O) linked to N(Et) and N-methylpyrrolidine) | ES: 240. |

Example 1

2-Chloro-N-(4-chloro-2-fluorophenyl)-6,7-dimethoxyquinazoline-4-amine hydrochloride (405 mg), N,1-dimethyl-N-piperidin-4-yl-L-prolinamide dihydrochloride (447 mg) and 1,8-diazabicyclo[5.4.0]undec-7-ene (608 mg) were added to 1,4-dioxane (20 mL), followed by heating under reflux for 24 hours. After concentration of the reaction solution, ethyl acetate and water were added to the residue, the organic layer was separated, and the water layer was further extracted with ethyl acetate. The combined organic layer was washed with saturated brine, dried over magnesium sulfate and then filtered. The solvent was evaporated under a reduced pressure. By purifying the residue by silica gel flash column chromatography (chloroform-MeOH), N-(1-{4-[(4-chloro-2-fluorophenyl)amino]-6,7-dimethoxyquinazolin-2-yl}piperidin-4-yl)-N,1-dimethyl-L-prolinamide was obtained. This was dissolved in ethyl acetate (10 mL), and 4 M HCl/ethyl acetate solution (0.5 mL) was added thereto. By evaporating the solvent under a reduced pressure and recrystallizing the resulting residue from EtOH-diethyl ether, N-(1-{4-[(4-chloro-2-fluorophenyl)amino]-6,7-dimethoxyquinazolin-2-yl}piperidin-4-yl)-N,1-dimethyl-L-prolinamide dihydrochloride (155 mg) was obtained as pale yellow powder.

Example 2

N-(4-chloro-2-fluorophenyl)-6,7-dimethoxy-2-[4-(methylamino)piperidin-1-yl]quinazoline-4-amine (445 mg), 1-(tert-butoxycarbonyl)-L-proline (323 mg), HOBt (135 mg) and EDCI hydrochloride (290 mg) were added in that order to DMF (10 mL), followed by stirring at room temperature for 24 hours. Ethyl acetate and a saturated sodium bicarbonate aqueous solution were added to the reaction solution, and the organic layer was separated. Next, the organic layer was washed with saturated brine, dried over magnesium sulfate and then filtered. The solvent was evaporated under a reduced pressure. By purifying the residue by silica gel flash column chromatography (chloroform-MeOH), N-(1-{4-[(4-chloro-2-fluorophenyl)amino]-6,7-dimethoxyquinazolin-2-yl}piperidin-4-yl)-N-methyl-L-prolinamide was obtained. This was dissolved in ethyl acetate (10 mL), and 4 M HCl/ethyl acetate solution (0.5 mL) was added thereto. By evaporating the solvent under a reduced pressure and recrystallizing the resulting residue from EtOH-diethyl ether, N-(1-{4-[(4-chloro-2-fluorophenyl)amino]-6,7-dimethoxyquinazolin-2-yl}piperidin-4-yl)-N-methyl-L-prolinamide dihydrochloride (481 mg) was obtained as pale yellow powder.

Example 3

Triethylamine (175 μl) and acetyl chloride (32 μl) were added under ice-cooling to a dichloromethane (5 mL) solution of N-(1-{4-[(4-chloro-2-fluorophenyl)amino]-6,7-dimethoxyquinazolin-2-yl}piperidin-4-yl)-N-methyl-L-prolinamide dihydrochloride (250 mg), followed by stirring under ice-cooling for 2 hours and under room temperature for 20 hours. A saturated sodium bicarbonate aqueous solution was added thereto, followed by extraction with chloroform. The organic layer was washed with saturated brine and dried over anhydrous sodium sulfate. Then, the solvent was evaporated. By purifying the resulting residue by a silica gel column chromatography (chloroform-MeOH), 1-acetyl-N-(1-{4-[(4-chloro-2-fluorophenyl)amino]-6,7-dimethoxyquinazolin-2-yl}piperidin-4-yl)-N-methyl-L-prolinamide was obtained. This compound was dissolved in MeOH (3 mL), 4 M HCl/ethyl acetate solution (203 μl) was added thereto, and the solvent was evaporated. By crystallizing the resulting crude crystals from isopropanol-diisopropyl ether, 1-acetyl-N-(1-{4-[(4-chloro-2-fluorophenyl)amino]-6,7-dimethoxyquinazolin-2-yl}piperidin-4-yl)-N-methyl-L-prolinamide hydrochloride (167 mg) was obtained as pale yellow crystals.

Example 4

Potassium carbonate (62 mg) and ethyl iodide (36 μl) were added in that order to an acetonitrile (5 mL) solution of N-(1-{4-[(4-chloro-2-fluorophenyl)amino]-6,7-dimethoxyquinazolin-2-yl}piperidin-4-yl)-N-methyl-L-prolinamide dihydrochloride (250 mg), followed by stirring at room temperature for 2 hours and at 50° C. for 19 hours. The solvent was evaporated, and a saturated sodium bicarbonate aqueous solution was added to the resulting residue, followed by extraction with chloroform. The organic layer was washed with saturated brine and dried over anhydrous sodium sulfate. Then, the solvent was evaporated. By purifying the resulting residue by a silica gel column chromatography (chloroform-MeOH), N-(1-{4-[(4-chloro-2-fluorophenyl)amino]-6,7-dimethoxyquinazolin-2-yl}piperidin-4-yl)-1-ethyl-N-methyl-L-prolinamide was obtained. This compound was dissolved in MeOH (3 mL), 4 M HCl/ethyl acetate solution (198 μl) was added thereto, and the solvent was evaporated. By recrystallizing the resulting crude crystals from isopropanol-diisopropyl ether, N-(1-{4-[(4-chloro-2-fluorophenyl)amino]-6,7-dimethoxyquinazolin-2-yl}piperidin-4-yl)-1-ethyl-N-methyl-L-prolinamide dihydrochloride (101 mg) was obtained as pale yellow crystals.

The compounds shown in the following Table 6 to Table 21 were produced in the same manner as in any one of Examples 1 to 4 using corresponding materials.

In this connection, symbols in the tables represent the following meanings (the same shall apply hereinafter).

Ex: Example number.

$R^A$, $R^B$, $R^C$, $R^D$, $R^E$: Substituents in general formula (cPr: cyclopropyl, cBu: cyclobutyl, Ph: phenyl, Bn: benzyl, Py: pyridyl, Ac: acetyl, Ms: methanesulfonyl, di: di, tri: tri. Also, the numeral before substituent indicates its substitution position. Accordingly, for example, 2-F-4-Cl-Ph means 2-fluoro-4-chlorophenyl, and 3,5-diCl-2-Py 3,5-dichloropyridin-2-yl).

Syn: Shows that it was produce using the corresponding material in the same manner as in the example of its number.

TABLE 6

| Ex | R^A | R^B | R^C | R^D | R^E | Syn | Data |
|---|---|---|---|---|---|---|---|
| 1 | OMe | OMe | 2-F-4-Cl-Ph | Me | (S)-1-Me-pyrrolidin-2-yl | 1 | F: 557. NMR: 8.17(1 H, brs), 7.41 (1 H, d, J = 8.3 Hz), 3.92 (3 H, s), 3.91(3 H, s). |
| 2 | OMe | OMe | 2-F-4-Cl-Ph | Me | (S)-pyrrolidin-2-yl | 2 | F: 543. |
| 3 | OMe | OMe | 2-F-4-Cl-Ph | Me | (S)-1-Ac-pyrrolidin-2-yl | 3 | F: 585. |
| 4 | OMe | OMe | 2-F-4-Cl-Ph | Me | (S)-1-Et-pyrrolidin-2-yl | 4 | F: 571. |
| 5 | H | CN | 2-F-4-Cl-Ph | Me | (S)-pyrrolidin-2-yl | 2 | ES: 508. |
| 6 | F | OMe | 2-F-4-Cl-Ph | Me | (S)-1-Me-pyrrolidin-2-yl | 1 | F: 545. |
| 7 | Br | H | 2-F-4-Cl-Ph | Me | (S)-1-Me-pyrrolidin-2-yl | 1 | ES: 577. |

TABLE 7

| Ex | R^A | R^B | R^C | R^D | R^E | Syn | Data |
|---|---|---|---|---|---|---|---|
| 8 | OMe | OMe | 2-F-4-Cl-Ph | H | (S)-pyrrolidin-2-yl | 2 | F: 529. |
| 9 | OMe | OMe | 2-F-4-Cl-Ph | Et | (S)-pyrrolidin-2-yl | 2 | F: 557. |
| 10 | OMe | OMe | 2-F-4-Cl-Ph | Me | (R)-pyrrolidin-2-yl | 2 | ES: 543. |
| 11 | OMe | OMe | 2-F-4-Cl-Ph | Me | (S)-1-Ms-pyrrolidin-2-yl | 3 | F: 621. |
| 12 | OMe | OMe | 2-F-4-Cl-Ph | Et | (R)-pyrrolidin-2-yl | 2 | F: 557. NMR: 8.17(1 H, br s), 7.41(1 H, d, J = 8.3 Hz), 3.91(3 H, s), 1.02 (3 H, t, J = 6.4 Hz). |
| 13 | OMe | OMe | 2-F-4-Cl-Ph | cPr | (S)-pyrrolidin-2-yl | 2 | F: 569. NMR: 8.15(1 H, br s), 7.41(1 H, dd, J = 1.6, 8.8 Hz), 3.92(3 H, s), 0.87(2 H, m). |
| 14 | OMe | OMe | 2-F-4-Cl-Ph | cPr | (R)-pyrrolidin-2-yl | 2 | F: 569. |

TABLE 8
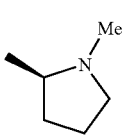
| Ex | R$^A$ | R$^B$ | R$^C$ | R$^D$ | R$^E$ | Syn | Data |
|---|---|---|---|---|---|---|---|
| 15 | H | CN | 2-F-4-Cl-Ph | Me | 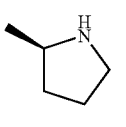 | 1 | F: 522. |
| 16 | OMe | OMe | 2-F-4-Cl-Ph | cBu | 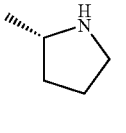 | 2 | ES: 583. |
| 17 | OMe | OMe | 2-F-4-Cl-Ph | cBu | 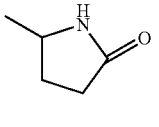 | 2 | ES: 583. |
| 18 | OMe | OMe | 2-F-4-Cl-Ph | Me | 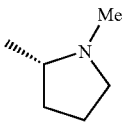 | 2 | ES: 557. |
| 19 | OMe | OMe | 2-F-4-Cl-Ph | Me | 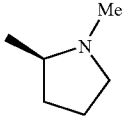 | 2 | F: 557. |
| 20 | OMe | OMe | 2-F-4-Cl-Ph | cPr | 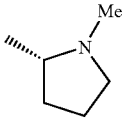 | 2 | F: 583. |
| 21 | OMe | OMe | 2-F-4-Cl-Ph | cPr | 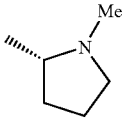 | 2 | F: 583. NMR: 8.19(1 H, br s), 7.40(1 H, dd, J = 1.2, 8.8 Hz), 3.91(3 H, s), 0.88(2 H, m). |

TABLE 9

[Structure: quinazoline with R^A, R^B on benzene ring, HN-R^C at 4-position, piperidine at 2-position bearing N(R^D)C(=O)R^E]

| Ex | R^A | R^B | R^C | R^D | R^E | Syn | Data |
|---|---|---|---|---|---|---|---|
| 22 | Br | H | 2-F-4-Cl-Ph | Me | (2S)-1-methylpyrrolidin-2-yl | 1 | ES: 575. NMR: 8.97(1 H, br s), 7.42(1 H, d, J = 7.6 Hz), 2.76(3 H, s). |
| 23 | H | CN | 2-F-4-Cl-Ph | Et | (2S)-1-methylpyrrolidin-2-yl | 1 | ES: 536. |
| 24 | H | CN | 2-F-4-Cl-Ph | Et | (2R)-1-methylpyrrolidin-2-yl | 1 | ES: 536. |
| 25 | OMe | OMe | 2-F-4-Cl-Ph | Et | (2S)-1-methylpyrrolidin-2-yl | 1 | ES: 571. |
| 26 | OMe | OMe | 2-F-4-Cl-Ph | Et | (2R)-1-methylpyrrolidin-2-yl | 1 | ES: 571. |
| 27 | Br | H | 2-F-4-Cl-Ph | Me | (2R)-pyrrolidin-2-yl | 1 | ES: 561. |
| 28 | H | CN | 2-F-4-Cl-Ph | Et | (2R)-pyrrolidin-2-yl | 1 | F: 522. NMR: 8.74(1 H, br s), 7.42(1 H, d, J = 8.0 Hz), 1.72(4 H, m), 1.02 (3 H, t, J = 7.6 Hz). |

TABLE 10
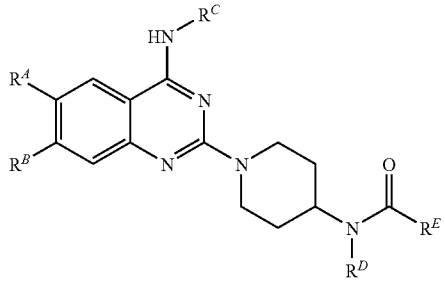
| Ex | R$^A$ | R$^B$ | R$^C$ | R$^D$ | R$^E$ | Syn | Data |
|---|---|---|---|---|---|---|---|
| 29 | F | H | 2-F-4-Cl-Ph | Me | 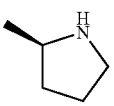 | 1 | ES: 501.<br>NMR: 8.55(1 H, br s), 7.43(1 H, d, J = 8.0 Hz), 1.91(2 H, m), 1.73 (2 H, m). |
| 30 | F | H | 2-F-4-Cl-Ph | Me | 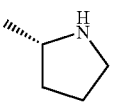 | 1 | ES: 501.<br>NMR: 8.56(1 H, br s), 7.43(1 H, d, J = 8.3 Hz), 1.91(2 H, m), 1.73 (2 H, m). |
| 31 | F | H | 2-F-4-Cl-Ph | Me | 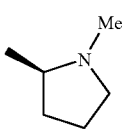 | 1 | ES: 515.<br>NMR: 8.59(1 H, d, J = 7.6 Hz), 7.43(1 H, d, J = 8.8 Hz), 3.60(1 H, m), 2.10(1 H, m). |
| 32 | F | H | 2-F-4-Cl-Ph | Me | 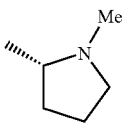 | 1 | ES: 515.<br>NMR: 8.60(1 H, d, J = 7.6 Hz), 7.43(1 H, d, J = 8.8 Hz), 3.60(1 H, m), 2.09(1 H, m). |
| 33 | F | H | 2-F-4-Cl-Ph | Et | 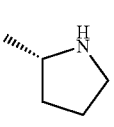 | 1 | ES: 515. |
| 34 | OMe | F | 2-F-4-Cl-Ph | Me | 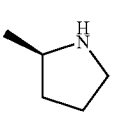 | 1 | ES: 531. |

TABLE 11
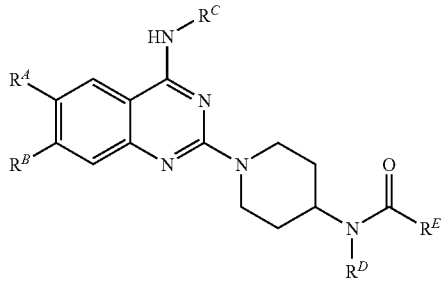
| Ex | R$^A$ | R$^B$ | R$^C$ | R$^D$ | R$^E$ | Syn | Data |
|---|---|---|---|---|---|---|---|
| 35 | OMe | F | 2-F-4-Cl-Ph | Me | 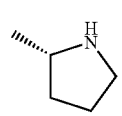 | 1 | F: 531. |
| 36 | OMe | F | 2-F-4-Cl-Ph | Me | 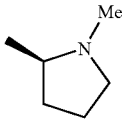 | 1 | F: 545. |
| 37 | OMe | F | 2-F-4-Cl-Ph | Me | 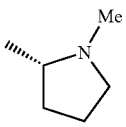 | 1 | F: 545.<br>NMR: 8.58(1 H, d, J = 8.0 Hz), 7.43(1 H, d, J = 8.8 Hz), 4.02 (3 H, s), 2.81(3 H, s). |
| 38 | F | H | 4-Cl-Ph | Me | 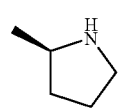 | 1 | F: 483. |
| 39 | F | H | 4-Cl-Ph | Me | 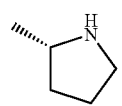 | 1 | F: 483. |
| 40 | F | H | 4-Cl-Ph | Et | 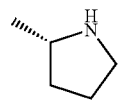 | 1 | F: 497.<br>NMR: 8.67(1 H, br s), 8.23(1 H, s), 7.54 (2 H, d, J = 8.8 Hz), 1.03 (3 H, t, J = 5.6 Hz). |
| 41 | F | H | 4-Cl-Ph | Me | 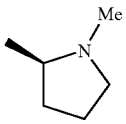 | 1 | F: 497. |

TABLE 12

![Structure: quinazoline with R^A, R^B substituents, HN-R^C at 4-position, piperidine at 2-position, piperidine bearing N(R^D)-C(=O)-R^E]

| Ex | R^A | R^B | R^C | R^D | R^E | Syn | Data |
|----|-----|-----|-----|-----|-----|-----|------|
| 42 | F | H | 4-Cl-Ph | Me | (S)-1-methylpyrrolidin-2-yl | 1 | F: 498. |
| 43 | Br | H | 4-Cl-Ph | Me | (R)-pyrrolidin-2-yl | 1 | F: 545. |
| 44 | Br | H | 4-Cl-Ph | Me | (S)-pyrrolidin-2-yl | 1 | F: 545. |
| 45 | Br | H | 4-Cl-Ph | Et | (S)-pyrrolidin-2-yl | 1 | F: 559. |
| 46 | Br | H | 4-Cl-Ph | Me | (R)-1-methylpyrrolidin-2-yl | 1 | F: 559. NMR: 9.01 (1 H, s), 7.53 (2 H, d, J = 8.8 Hz), 2.82 (3 H, s), 2.02 (1 H, m). |
| 47 | Br | H | 4-Cl-Ph | Me | (S)-1-methylpyrrolidin-2-yl | 1 | F: 559. NMR: 9.02 (1 H, s), 7.53 (2 H, d, J = 8.8 Hz), 2.82 (3 H, s), 2.03 (1 H, m). |
| 48 | F | H | 2-F-4-Cl-Ph | Et | (S)-pyrrolidin-2-yl | 1 | F: 515. |

TABLE 13

![Structure: same scaffold as Table 12]

| Ex | R^A | R^B | R^C | R^D | R^E | Syn | Data |
|----|-----|-----|-----|-----|-----|-----|------|
| 49 | F | H | 2-F-4-Cl-Ph | Et | (R)-1-methylpyrrolidin-2-yl | 1 | F: 529. |
| 50 | F | H | 2-F-4-Cl-Ph | Et | (S)-1-methylpyrrolidin-2-yl | 1 | F: 529. |
| 51 | F | H | 4-Cl-Ph | Et | (R)-1-methylpyrrolidin-2-yl | 1 | F: 511. |
| 52 | F | H | 4-Cl-Ph | Et | (S)-1-methylpyrrolidin-2-yl | 1 | F: 511. |
| 53 | F | H | 4-Cl-Ph | Et | pyrrolidin-2-yl | 1 | ES: 497. |
| 54 | Br | H | 2-F-4-Cl-Ph | Me | pyrrolidin-2-yl | 1 | ES: 561. NMR: 8.92 (1 H, s), 7.43 (1 H, d, J = 8.4 Hz), 4.52 (1 H, m), 1.92 (2 H, m). |
| 55 | Br | H | 2-F-4-Cl-Ph | Et | pyrrolidin-2-yl | 1 | F: 577. |

TABLE 14

Structure: quinazoline with R^A, R^B on benzene ring; 4-position HN-R^C; 2-position linked to piperidine N; piperidine 4-position has N(R^D)-C(=O)-R^E

| Ex | R^A | R^B | R^C | R^D | R^E | Syn | Data |
|---|---|---|---|---|---|---|---|
| 56 | Br | H | 2-F-4-Cl-Ph | Et | (S)-pyrrolidin-2-yl | 1 | F: 577. |
| 57 | Br | H | 2-F-4-Cl-Ph | Et | (S)-1-Me-pyrrolidin-2-yl | 1 | ES: 589. |
| 58 | Br | H | 2-F-4-Cl-Ph | Et | (R)-1-Me-pyrrolidin-2-yl | 1 | ES: 591. |
| 59 | Br | H | 4-Cl-Ph | Et | (S)-1-Me-pyrrolidin-2-yl | 1 | ES: 573. |
| 60 | Br | H | 4-Cl-Ph | Et | (R)-1-Me-pyrrolidin-2-yl | 1 | F: 573. |
| 61 | F | OMe | 2-F-4-Cl-Ph | Me | (S)-pyrrolidin-2-yl | 1 | F: 531. NMR: 8.62 (1 H, d, J = 10.8 Hz), 7.41 (1 H, d, J = 8.8 Hz), 3.98 (3 H, s), 1.91 (2 H, m). |
| 62 | F | OMe | 2-F-4-Cl-Ph | Me | (R)-pyrrolidin-2-yl | 1 | F: 531. NMR: 8.62 (1 H, d, J = 12.0 Hz), 7.41 (1 H, d, J = 8.8 Hz), 3.98 (3 H, s), 1.91 (2 H, m). |

TABLE 15

Structure: same quinazoline-piperidine-amide scaffold as Table 14.

| Ex | R^A | R^B | R^C | R^D | R^E | Syn | Data |
|---|---|---|---|---|---|---|---|
| 63 | F | OMe | 2-F-4-Cl-Ph | Et | (S)-pyrrolidin-2-yl | 1 | ES: 545. |
| 64 | Br | H | 4-Cl-Ph | Et | (S)-pyrrolidin-2-yl | 1 | ES: 559. |
| 65 | F | OMe | 2-F-4-Cl-Ph | Et | (R)-pyrrolidin-2-yl | 1 | ES: 545. NMR: 8.59 (1 H, m), 7.41 (1 H, dd, J = 2.0, 8.8 Hz), 3.99 (3 H, s), 1.02 (3 H, t, J = 6.8 Hz,). |
| 66 | F | OMe | 2-F-4-Cl-Ph | Me | (R)-1-Me-pyrrolidin-2-yl | 1 | ES: 545. NMR: 8.71 (1 H, d, J = 11.6 Hz), 7.41 (1 H, d, J = 8.8 Hz), 3.98 (3 H, s), 2.81 (3 H, s). |
| 67 | F | OMe | 2-F-4-Cl-Ph | Et | (R)-1-Me-pyrrolidin-2-yl | 1 | ES: 557. NMR: 8.64 (1 H, d, J = 11.2 Hz), 7.41 (1 H, dd, J = 2.0, 8.8 Hz), 3.99 (3 H, s), 1.03 (3 H, t, J = 6.4 Hz). |
| 68 | H | CN | 2-F-4-Cl-Ph | Me | (R)-pyrrolidin-2-yl | 1 | ES: 508. NMR: 8.81 (1 H, s), 7.43 (1 H, d, J = 8.4 Hz), 4.52 (2 H, m), 1.91 (2 H, m). |

TABLE 16

[Structure: quinazoline with R^A, R^B substituents, HN-R^C at 4-position, and 2-position connected to piperidine bearing N(R^D)-C(=O)-R^E]

| Ex | R^A | R^B | R^C | R^D | R^E | Syn | Data |
|---|---|---|---|---|---|---|---|
| 69 | H | CN | 2-F-4-Cl-Ph | Et | (S)-2-methylpyrrolidinyl | 1 | ES: 522. |
| 70 | H | CN | 2-F-4-Cl-Ph | Me | (S)-1,2-dimethylpyrrolidinyl | 1 | ES: 522. |
| 71 | F | H | 2-F-4-Cl-Ph | Me | (S)-2-methyl-1-(3-hydroxypropyl)pyrrolidinyl | 4 | ES: 559. |
| 72 | F | OMe | 2,4,5-triF-Ph | Me | (S)-pyrrolidin-2-yl | 1 | ES: 533. |

TABLE 16-continued

| Ex | R^A | R^B | R^C | R^D | R^E | Syn | Data |
|---|---|---|---|---|---|---|---|
| 73 | F | OMe | 4-Cl-Ph | Me | (S)-pyrrolidin-2-yl | 1 | ES: 513. |
| 74 | F | OMe | 5-Cl-2-Py | Me | (S)-pyrrolidin-2-yl | 1 | ES: 514. |
| 75 | F | OMe | 3,5-diCl-2-Py | Me | (S)-pyrrolidin-2-yl | 1 | ES: 548. |
| 76 | F | OMe | 5-F-2-Py | Me | (S)-pyrrolidin-2-yl | 1 | ES: 498. |

TABLE 17

[Structure: quinazoline with R^A, R^B substituents, HN-R^C at 4-position, and 2-position connected to piperidine bearing N(R^D)-C(=O)-R^E]

| Ex | R^A | R^B | R^C | R^D | R^E | Syn | Data |
|---|---|---|---|---|---|---|---|
| 77 | F | OMe | 2-F-4-Cl-Ph | Me | (S)-2-(2-hydroxyethyl)pyrrolidinyl | 4 | ES: 575. |
| 78 | F | OMe | 2,6-diF-4-Cl-Ph | Me | (S)-pyrrolidin-2-yl | 1 | ES: 549. |

TABLE 17-continued

| Ex | R^A | R^B | R^C | R^D | R^E | Syn | Data |
|---|---|---|---|---|---|---|---|
| 79 | F | OMe | 2-F-4-Cl-Bn | Me | (S)-pyrrolidin-2-yl | 1 | ES: 545. NMR (DMSO-d6): 7.41 (1 H, dd, J = 1.8, 8.3 Hz), 4.78-4.70 (2 H, m), 4.60-4.48 1 H, m), 3.94 (3 H, s). |
| 80 | F | OMe | 2-F-4-Cl-Ph | Me | (S)-2-(2,3-dihydroxypropyl)pyrrolidin-2-yl | 4 | ES: 605. |
| 81 | F | OMe | 2-F-4-Cl-Ph | Me | 3,3-dimethylpyrrolidin-2-yl | 2 | ES: 559. |
| 82 | F | OMe | 2-F-4-Cl-Ph | Me | (2S,4R)-4-hydroxy-2-methylpyrrolidin-2-yl | 2 | ES: 547. |

TABLE 18

| Ex | R^A | R^B | R^C | R^D | R^E | Syn | Data |
|---|---|---|---|---|---|---|---|
| 83 | F | OMe | 2-F-4-Cl-Ph | Me | (2S,4S)-4-hydroxy-pyrrolidin-2-yl | 2 | ES: 547. |

TABLE 18-continued
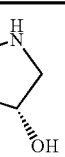
| Ex | R^A | R^B | R^C | R^D | R^E | Syn | Data |
|----|-----|-----|-----|-----|-----|-----|------|
| 84 | F | OMe | 2-F-4-Cl-Ph | Me | 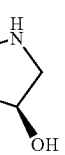 | 2 | ES: 547. |
| 85 | F | OMe | 2-F-4-Cl-Ph | Me | 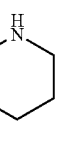 | 2 | ES: 547. |
| 86 | OMe | OMe | 2-F-4-Cl-Ph | Me | 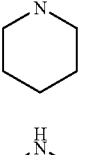 | 2 | F: 557. |
| 87 | OMe | OMe | 2-F-4-Cl-Ph | Me | 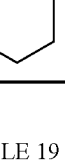 | 2 | ES: 557. |
| 88 | OMe | OMe | 2-F-4-Cl-Ph | Et | 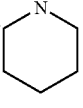 | 2 | F: 571.<br>NMR: 8.18 (1 H, br s), 7.41 (1 H, d, J = 7.2 Hz), 3.92 (3 H, s), 1.00 (3 H, t, J = 6.8 Hz). |
TABLE 19
| Ex | R^A | R^B | R^C | R^D | R^E | Syn | Data |
|----|-----|-----|-----|-----|-----|-----|------|
| 89 | OMe | OMe | 2-F-4-Cl-Ph | Et | | 2 | F: 571.<br>NMR: 8.16 (1 H, br s), 7.41 (1 H, d, J = 7.6 Hz), 3.92 (3 H, s), 1.00 (3 H, t, J = 6.8 Hz). |

TABLE 19-continued

| Ex | $R^A$ | $R^B$ | $R^C$ | $R^D$ | $R^E$ | Syn | Data |
|---|---|---|---|---|---|---|---|
| 90 | OMe | OMe | 2-F-4-Cl-Ph | cPr | (S)-piperidin-2-yl | 2 | F: 583. NMR: 8.10 (1 H, br s), 7.42 (1 H, dd, J = 1.2, 8.8 Hz), 3.92 (6 H, s), 0.86 (2 H, m). |
| 91 | OMe | OMe | 2-F-4-Cl-Ph | cBu | (S)-piperidin-2-yl | 2 | ES: 597. |
| 92 | OMe | OMe | 2-F-4-Cl-Ph | Me | (S)-azetidin-2-yl | 2 | F: 543. |

TABLE 20

| Ex | $R^A$ | $R^C$ | $R^E$ | Syn | Data |
|---|---|---|---|---|---|
| 93 | Et | 2-F-4-Cl-Ph | (S)-1-methylpyrrolidin-2-yl | 2 | ES: 515. |
| 94 | Me | 2-F-4-Cl-Ph | (S)-pyrrolidin-2-yl | 2 | F: 487. |
| 95 | Me | 2-F-4-Cl-Ph | (R)-pyrrolidin-2-yl | 2 | F: 487. |
| 96 | Me | 2-F-4-Cl-Ph | (S)-1-methylpyrrolidin-2-yl | 2 | F: 501. |
| 97 | Me | 2-F-4-Cl-Ph | (R)-1-methylpyrrolidin-2-yl | 2 | F: 501. |
| 98 | Et | 2-F-4-Cl-Ph | (S)-pyrrolidin-2-yl | 2 | F: 501. NMR: 9.80 (1 H, d, J = 7.6 Hz), 7.32 (1 H, d, J = 8.8 Hz), 1.91 (2 H, m), 1.34 (3 H, dt, J = 2.0, 7.6 Hz). |

TABLE 20-continued

Structure: pyrazolo[3,4-d]pyrimidine with HN-R^C at 4-position, R^A on pyrazole N, piperidine with N(Me)C(O)R^E at 6-position.

| Ex | R^A | R^C | R^E | Syn | Data |
|---|---|---|---|---|---|
| 99 | Et | 2-F-4-Cl-Ph | (S)-pyrrolidin-2-yl (NH) | 2 | F: 501. NMR: 9.76 (1 H, d, J = 6.4 Hz), 7.31 (1 H, d, J = 8.8 Hz), 1.92 (2 H, m), 1.34 (3 H, dt, J = 2.0, 7.6). |
| 100 | Et | 2-F-4-Cl-Ph | (S)-1-Me-pyrrolidin-2-yl | 2 | F: 515. |

TABLE 21

| Ex | R^A | R^C | R^E | Syn | Data |
|---|---|---|---|---|---|
| 101 | —CH$_2$CF$_3$ | 2-F-4-Cl-Ph | (S)-pyrrolidin-2-yl (NH) | 2 | F: 555. NMR: 9.92 (1 H, d, J = 5.6 Hz), 7.32 (1 H, m), 5.02 (2 H, m), 1.91 (2 H, m). |
| 102 | —CH$_2$CF$_3$ | 2-F-4-Cl-Ph | (R)-pyrrolidin-2-yl (NH) | 2 | F: 555. NMR: 9.89 (1 H, d, J = 5.6 Hz), 7.32 (1 H, m), 5.02 (2 H, m), 1.92 (2 H, m). |
| 103 | —CH$_2$CF$_3$ | 2-F-4-Cl-Ph | (S)-1-Me-pyrrolidin-2-yl | 2 | F: 569. NMR: 9.95 (1 H, d, J = 10.0 Hz), 7.32 (1 H, dd, J = 1.6, 8.4 Hz), 5.03 (2 H, m), 2.79 (3 H, s). |
| 104 | —CH$_2$CF$_3$ | 2-F-4-Cl-Ph | (R)-1-Me-pyrrolidin-2-yl | 2 | F: 569. NMR: 9.98 (1 H, d, J = 10.4 Hz), 7.32 (1 H, dd, J = 1.6, 8.8 Hz), 5.03 (2 H, m), 2.79 (3 H, s). |
| 105 | Et | 2-F-4-Cl-Bn | (S)-pyrrolidin-2-yl (NH) | 2 | ES: 515. |
| 106 | —CH$_2$CF$_3$ | 2-F-4-Cl-Bn | (S)-pyrrolidin-2-yl (NH) | 2 | ES: 569. |

Structures of other compounds of the present invention are shown in the following Table 22 to Table 26. These can be easily produced using the methods described in the above-mentioned Reference Examples and Examples and the methods which are obvious for those skilled in the art or modified methods thereof. In this connection, symbols in the tables represent the following meanings.

No: Compound number.

Str: Chemical structure.

TABLE 22

| No | Str |
|---|---|
| A1 | 4-(2-Br-4-Cl-phenylamino)-6-fluoro-2-[4-(N-methyl-(1-methylpyrrolidin-2-yl)carboxamido)piperidin-1-yl]quinazoline |

TABLE 22-continued
| No | Str |
|---|---|
| A2 | 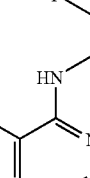 |
| A3 | |
| A4 | |
| A5 | |
| A6 | 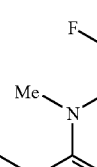 |
| A7 | |
| A8 | |
| A9 | |

TABLE 22-continued
| No | Str |
|---|---|
| A10 | 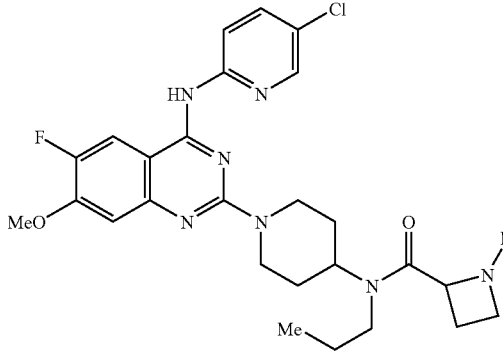 |
TABLE 23
| No | Str |
|---|---|
| A11 | 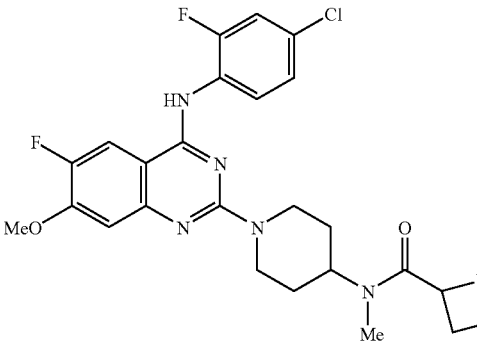 |
| A12 | 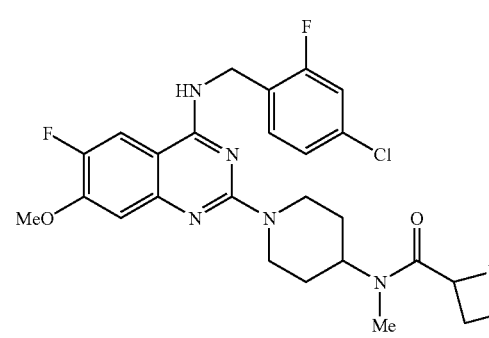 |
| A13 | 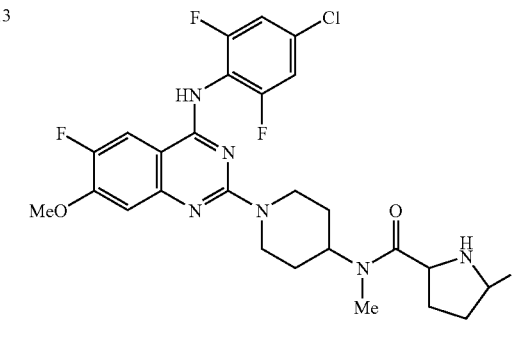 |
TABLE 23-continued
| No | Str |
|---|---|
| A14 | 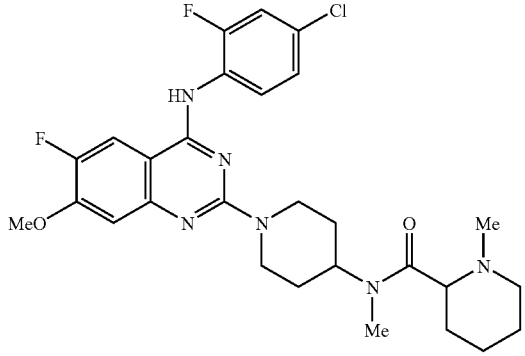 |
| A15 | 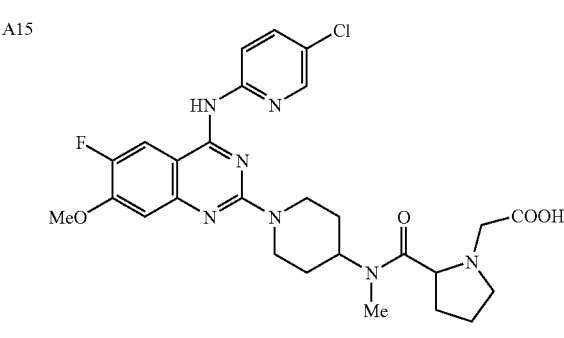 |
| A16 | 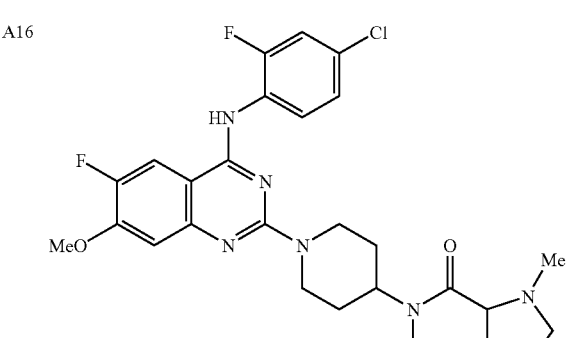 |
| A17 | 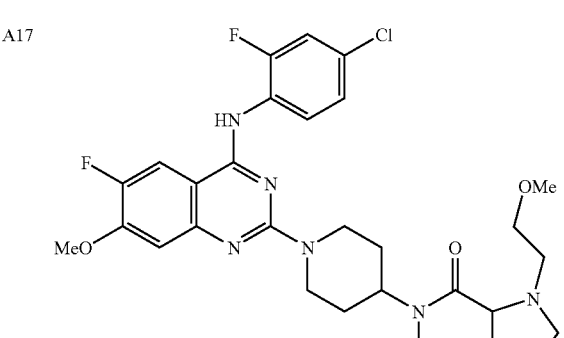 |

TABLE 23-continued
| No | Str |
|---|---|
| A18 | 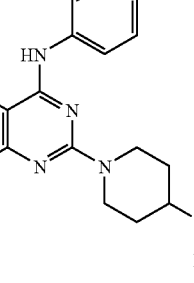 |
| A19 | 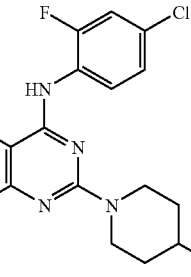 |
| A20 | 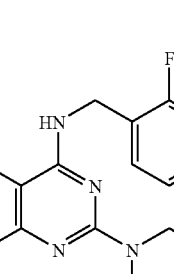 |
TABLE 24
| No | Str |
|---|---|
| A21 | 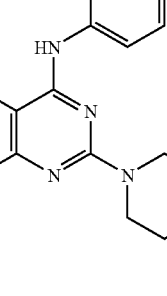 |
| A22 | 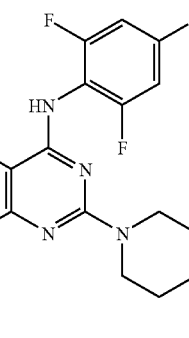 |
| A23 | 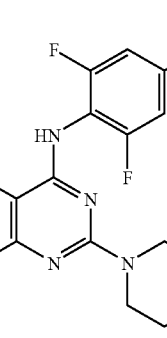 |
| A24 |  |
| A25 |  |

TABLE 24-continued

| No | Str |
|----|-----|
| A26 | (structure) |
| A27 | (structure) |
| A28 | (structure) |
| A29 | (structure) |
| A30 | (structure) |

TABLE 25

| No | Str |
|----|-----|
| A31 | (structure) |
| A32 | (structure) |

TABLE 25-continued

| No | Str |
|---|---|
| A33 | |
| A34 | |
| A35 | |
| A36 | |
| A37 | |
| A38 | |
| A39 | |
| A40 | |

TABLE 26
| No | Str |
|---|---|
| A41 | 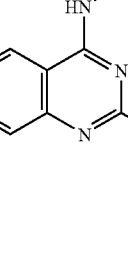 |
| A42 | |
| A43 | |
| A44 | |
TABLE 26-continued
| No | Str |
|---|---|
| A45 | 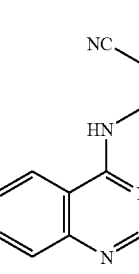 |
| A46 | |
| A47 | |
| A48 | |

TABLE 26-continued

| No | Str |
|---|---|
| A49 | 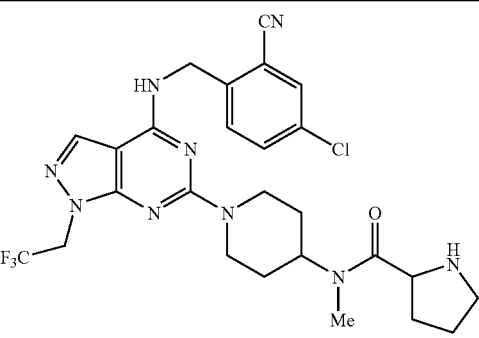 |
| A50 | 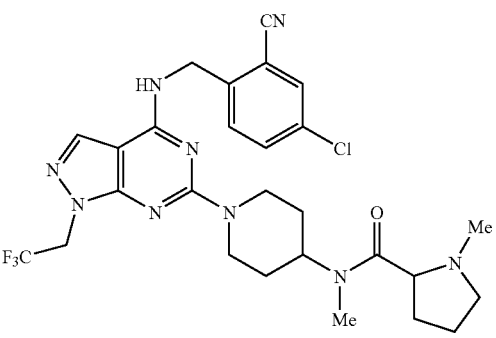 |

The invention claimed is:

1. A compound represented by a formula (I) or a pharmaceutically acceptable salt thereof

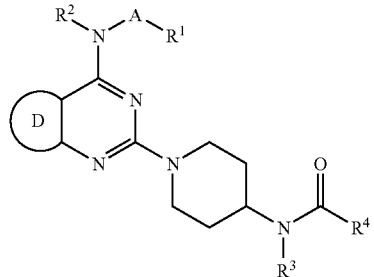

(I)

symbols in the formula represent the following meanings;

A: single bond or $C_1$-$C_6$ alkylene, $R^1$: phenyl or pyridyl, each of which may be substituted with halogen or cyano which may be substituted, $R^2$: —H or $C_1$-$C_6$ alkyl, $R^3$: —H, $C_1$-$C_6$ alkyl or $C_3$-$C_8$ cycloalkyl, $R^4$: azetidin-2-yl, pyrrolidin-2-yl or piperidin-2-yl, each of which may be substituted with —OH, —O—$C_1$-$C_6$ alkyl, oxo (=O), —$SO_2$—$C_1$-$C_6$ alkyl, or $C_1$-$C_6$ alkyl which may be substituted with —OH, —O—$C_1$-$C_6$ alkyl, or oxo (=O), and D: a ring selected from the group consisting of the following rings, wherein in these rings, the carbon atoms and nitrogen atoms constituting the rings may respectively be substituted with halogen, cyano, —O—$C_1$-$C_6$ alkyl, or $C_1$-$C_6$ alkyl which may be substituted with —OH, —O—$C_1$-$C_6$ alkyl or halogen,

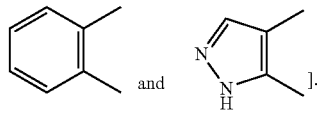

2. The compound according to claim 1 or a pharmaceutically acceptable salt thereof, —H and $R^4$ is pyrrolidin-2-yl which may be substituted with —OH, —O—$C_1$-$C_6$ alkyl, oxo (=O), —$SO_2$—$C_1$-$C_6$ alkyl, or $C_1$-$C_6$ alkyl which may be substituted with —OH, —O—$C_1$-$C_6$ alkyl, or oxo (=O).

* * * * *